US011484544B2

(12) United States Patent
Yang

(10) Patent No.: US 11,484,544 B2
(45) Date of Patent: Nov. 1, 2022

(54) PHARMACEUTICAL OR COSMETIC COMPOSITION FOR PREVENTING OR TREATING HAIR LOSS OR PROMOTING HAIR GROWTH

(71) Applicant: Mi Gyoung Yang, Seoul (KR)

(72) Inventor: Mi Gyoung Yang, Seoul (KR)

( * ) Notice: Subject to any disclaimer, the term of this patent is extended or adjusted under 35 U.S.C. 154(b) by 206 days.

(21) Appl. No.: 16/763,392

(22) PCT Filed: May 30, 2018

(86) PCT No.: PCT/KR2018/006140
§ 371 (c)(1),
(2) Date: May 12, 2020

(87) PCT Pub. No.: WO2019/093608
PCT Pub. Date: May 16, 2019

(65) Prior Publication Data
US 2021/0069228 A1 Mar. 11, 2021

(30) Foreign Application Priority Data
Nov. 13, 2017 (KR) .................. 10-2017-0150928

(51) Int. Cl.
*A61K 38/18* (2006.01)
*A61K 38/17* (2006.01)
*A61K 8/44* (2006.01)
*A61K 8/60* (2006.01)
*A61P 17/14* (2006.01)
*A61Q 5/02* (2006.01)
*A61Q 5/08* (2006.01)
*A61Q 5/12* (2006.01)
(Continued)

(52) U.S. Cl.
CPC .......... *A61K 31/7076* (2013.01); *A61K 8/345* (2013.01); *A61K 8/361* (2013.01); *A61K 8/44* (2013.01); *A61K 8/447* (2013.01); *A61K 8/492* (2013.01); *A61K 8/4913* (2013.01); *A61K 8/4946* (2013.01); *A61K 8/60* (2013.01); *A61K 8/606* (2013.01); *A61K 8/64* (2013.01); *A61K 8/673* (2013.01); *A61K 8/675* (2013.01); *A61K 8/676* (2013.01); *A61K 31/047* (2013.01); *A61K 31/198* (2013.01); *A61K 31/20* (2013.01); *A61K 31/201* (2013.01); *A61K 31/202* (2013.01); *A61K 31/375* (2013.01); *A61K 31/401* (2013.01); *A61K 31/405* (2013.01); *A61K 31/4172* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/52* (2013.01); *A61K 31/525* (2013.01); *A61K 31/714* (2013.01); *A61K 38/17* (2013.01); *A61K 38/18* (2013.01); *A61K 38/1808* (2013.01); *A61K 38/1825* (2013.01); *A61K 38/1858* (2013.01); *A61K 38/1866* (2013.01); *A61P 17/14* (2018.01); *A61Q 5/02* (2013.01); *A61Q 5/08* (2013.01); *A61Q 5/12* (2013.01); *A61Q 7/02* (2013.01)

(58) Field of Classification Search
CPC .............. A61K 2300/00; A61K 31/197; A61K 31/202; A61K 31/375; A61K 31/4188; A61K 31/455; A61K 31/51; A61K 31/519; A61K 31/5253; A61K 31/7084; A61K 31/714; A61K 38/063; A61K 38/1709; A61K 38/18; A61K 31/047; A61K 31/198; A61K 31/20; A61K 31/201; A61K 31/401; A61K 31/405; A61K 31/4172; A61K 31/4415; A61K 31/52; A61K 31/7076; A61K 38/17; A61K 38/1808; A61K 38/1825; A61K 38/1858; A61K 38/1866; A61K 8/345; A61K 8/361; A61K 8/44; A61K 8/442; A61K 8/447; A61K 8/4913; A61K 8/492; A61K 8/4946; A61K 8/4953; A61K 8/60; A61K 8/606; A61K 8/63; A61K 8/64; A61K 8/673; A61K 8/675; A61K 8/676; A61P 17/14; A61Q 5/02; A61Q 5/08; A61Q 5/12; A61Q 7/00; A61Q 7/02
See application file for complete search history.

(56) References Cited

U.S. PATENT DOCUMENTS

2010/0203055 A1* 8/2010 Imamura ............ A61K 31/7105
424/758
2012/0189607 A1 7/2012 Kim et al.
(Continued)

FOREIGN PATENT DOCUMENTS

KR 10-2003-0062605 A 7/2003
KR 1020030062005 A 7/2003
(Continued)

OTHER PUBLICATIONS

Non-Final OA for U.S. Appl. No. 17/042,580 "Pharmaceutical or Cosmetic Composition for Preventing or Treating Hair Loss or Promoting Hair Growth" dated Feb. 4, 2022.
(Continued)

*Primary Examiner* — Julie Ha
(74) *Attorney, Agent, or Firm* — Hamilton, Brook, Smith & Reynolds, P.C.

(57) ABSTRACT

A pharmaceutical composition or a cosmetic composition for treating hair loss, or promoting hair growth is described. The composition according to the present invention exhibits an excellent effect of treating hair loss and promoting hair growth, and can be safely used regardless of sex and age.

18 Claims, 1 Drawing Sheet

(51) Int. Cl.

| | |
|---|---|
| A61Q 7/02 | (2006.01) |
| A61Q 7/00 | (2006.01) |
| A61K 31/7076 | (2006.01) |
| A61K 8/34 | (2006.01) |
| A61K 8/36 | (2006.01) |
| A61K 8/49 | (2006.01) |
| A61K 8/64 | (2006.01) |
| A61K 8/67 | (2006.01) |
| A61K 31/047 | (2006.01) |
| A61K 31/198 | (2006.01) |
| A61K 31/20 | (2006.01) |
| A61K 31/201 | (2006.01) |
| A61K 31/202 | (2006.01) |
| A61K 31/375 | (2006.01) |
| A61K 31/401 | (2006.01) |
| A61K 31/405 | (2006.01) |
| A61K 31/4172 | (2006.01) |
| A61K 31/4188 | (2006.01) |
| A61K 31/4415 | (2006.01) |
| A61K 31/455 | (2006.01) |
| A61K 31/51 | (2006.01) |
| A61K 31/519 | (2006.01) |
| A61K 31/52 | (2006.01) |
| A61K 31/525 | (2006.01) |
| A61K 31/714 | (2006.01) |

(56) References Cited

U.S. PATENT DOCUMENTS

| | | |
|---|---|---|
| 2013/0224177 A1 | 8/2013 | Kim et al. |
| 2021/0015840 A1 | 1/2021 | Yang |

FOREIGN PATENT DOCUMENTS

| | | | |
|---|---|---|---|
| KR | 1020060059557 A | | 6/2006 |
| KR | 1020120014788 A | | 2/2012 |
| KR | 10-2015-0117609 A | | 10/2015 |
| KR | 1020150117609 | * | 10/2015 ............... A61K 8/60 |
| KR | 10-2016-0060914 A | | 5/2016 |
| KR | 1020160119690 A | | 10/2016 |
| KR | 10-2017-0008501 A | | 1/2017 |
| WO | 2019194470 | | 10/2019 |

OTHER PUBLICATIONS

Alopecia Areata from Merck Manual, pp. 1-3. Accessed Nov. 2, 2020. (Year: 2020).

Alopecia from Merck Manual, pp. 1-9. Accessed Nov. 2, 2020. (Year: 2020).

International Search Report for International Application No. PCT/KR2019/003638, "Pharmaceutical or Cosmetic Composition for Preventing or Treating Hair Loss or Promoting Hair Growth", dated Jul. 4, 2019.

Written Opinion for International Application No. PCT/KR2019/003638, "Pharmaceutical or Cosmetic Composition for Preventing or Treating Hair Loss or Promoting Hair Growth", dated Jul. 4, 2019.

Takahashi, J., et al., "Deficit of CD38/cyclic ADP-ribose is differentially compensated in hearts by gender", Biochemical and Biophysical Research Communications 312 (2003) 434-440.

Dippel, E., et al., "Distribution of Constitutive Nitric Oxide Synthase Immunoreactivity and NADPH-Diaphorase Activity in Murine Telogen and Anagen Skin", Nitric Oxide Synthase, 103(1): 112-115, Jul. 1994.

International Search Report for International Application No. PCT/KR2018/006140, "Pharmaceutical or Cosmetic Composition for Preventing or Treating Hair Loss or Promoting Hair Growth", dated: Sep. 5, 2018.

Written Opinion for International Search Report for International Application No. PCT/KR2018/006140, "Pharmaceutical or Cosmetic Composition for Preventing or Treating Hair Loss or Promoting Hair Growth", dated: Sep. 5, 2018.

Chini EN. et al., "CD38 is the major enzyme responsible for synthesis of nicotinic acid-adenine dinucleotide phosphate in mammalian tissues", Biochem J 362:125-130, 2002.

Berridge G. et al., "Metabolism of the novel Ca2+-mobilizing messenger nicotinic acid-adenine dinucleotide phosphate via a 2«-specific Ca2+-dependent phosphatase", Biochem. J., 365: 295-301, 2002.

Aarhus R. et al., "ADP-ribosyl Cyclase and CD38 Catalyze the Synthesis of a Calcium-mobilizing Metabolite from NADP" J Biol Chem., 270(51): 30327-30333, 1995.

Graeff, R., et al., Acidic Residues at the Active Sites of CD38 and ADP-ribosyl Cyclase Determine Nicotinic Acid Adenine Dinucleotide Phosphate (NAADP) Synthesis and Hydrolysis Activities:, The Journal of Biological Chemistry. 281 (39): 28951-7, Sep. 29, 2006.

Shuto, S., et al., "Total Synthesis of Cyclic ADP-carbocyclic-ribose, a Stable Mimic of Ca2+-Mobilizing Second : fMessenger Cyclic ADP-Ribose", J. Am. Chem. Soc., 2001, 123, 8750-5759.

International Preliminary Report on Patentability for International Application No. PCT/KR2019/003638, "Pharmaceutical or Cosmetic Composition for Preventing or Treating Hair Loss or Promoting Hair Growth", dated Oct. 6, 2020.

International Preliminary Report on Patentability for International Application No. PCT/KR2018/006140, "Pharmaceutical or Cosmetic Composition for Preventing or Treating Hair Loss or Promoting Hair Growth", dated May 19, 2020.

* cited by examiner

[Fig. 1]
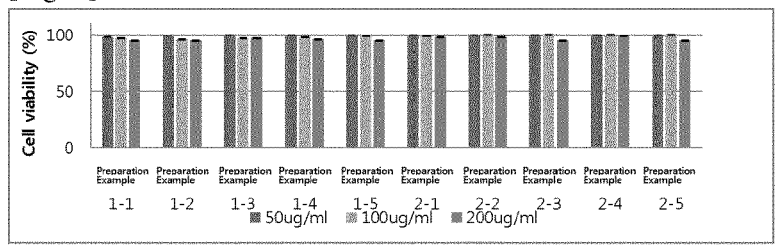
[Fig. 2]
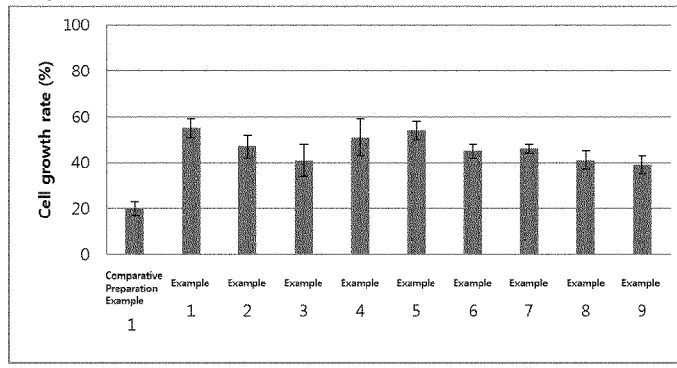
[Fig. 3]
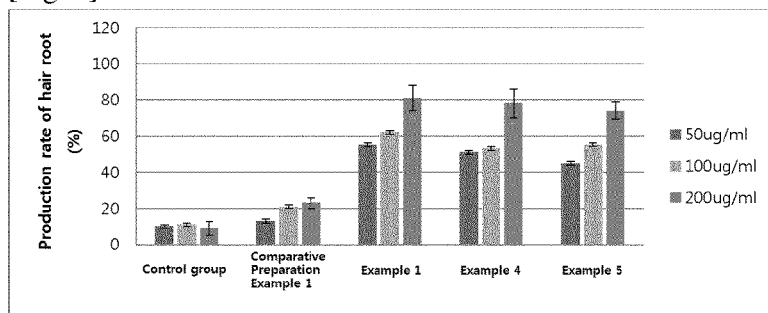
[Fig. 4]
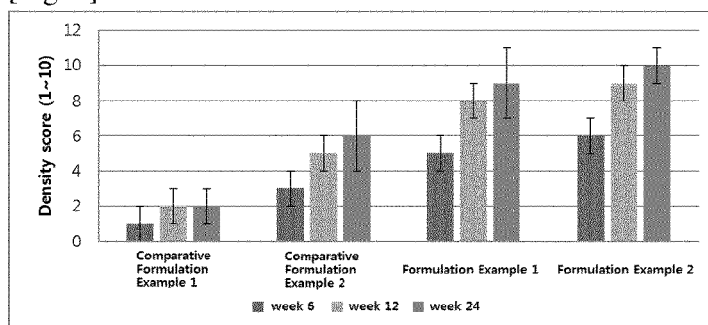
[Fig. 5]
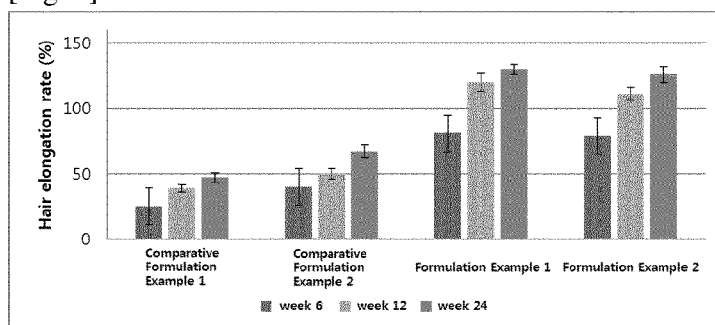

PHARMACEUTICAL OR COSMETIC COMPOSITION FOR PREVENTING OR TREATING HAIR LOSS OR PROMOTING HAIR GROWTH

This application is the U.S. National Stage of International Application No. PCT/KR2018/006140, filed May 30, 2018, which designates the U.S., published in English, and claims priority under 35 U.S.C. § 119 or 365(c) to Korea Application No. 10-2017-0150928, filed Nov. 13, 2017. The entire teachings of the above applications are incorporated herein by reference.

TECHNICAL FIELD

The present invention relates to a pharmaceutical composition or a cosmetic composition for preventing or treating hair loss, or promoting hair growth. More particularly, the present invention relates to a pharmaceutical composition or a cosmetic composition for preventing or treating hair loss, or promoting hair growth, comprising nicotinic acid adenine dinucleotide phosphate (NAADP), and at least one selected from the group comprising one or more nature-derived amino acid or salt thereof, one or more growth factor, noggin, one or more saturated or unsaturated C8 to C18 long chain fatty acid or salt thereof, one or more active factor and one or more water-soluble vitamin or salt thereof.

BACKGROUND ART

It has been known that hair loss is caused by local infections, endocrine disorders, genetic factors and autoimmunity as well as already known genetic causes. Recently, hair loss has been shown not only in middle-aged and elderly men but also in women or younger generation. Thus, as the need for prevention and treatment of such hair loss has increased, researches have been made on substances having various efficacy to overcome hair loss.

Drugs currently used to prevent or treat hair loss and promote hair growth include vasodilators to circulate enough blood in the scalp, an activity inhibitor inhibiting an activity of 5α-reductase that converts testosterone into 5-DHT(5-dihydrotestosterone), and the like. Examples of the vasodilator include minoxidil and the like, and examples of the 5-DHT activity inhibitor include finasteride, dutasteride, and the like. On the other hand, natural derivatives such as various plant extracts are also used in addition to the organic synthetic materials as described above, but the mechanism and effect thereof are not clearly revealed.

However, since the currently used preparations for preventing and treating hair loss and promoting hair growth are insufficient in their effects or have various problems such as side effects, it is necessary to develop a more effective and safe preparation for preventing or treating hair loss, or for promoting hair growth.

DISCLOSURE OF INVENTION

Technical Problem

The purpose of the present invention is to provide a safe pharmaceutical composition and a safe cosmetic composition that have an excellent effect in prevention or treatment of hair loss or promotion of hair growth and are applicable irrespective of age and sex.

Solution to Problem

In order to achieve the purpose above, the present invention provides a pharmaceutical composition and a cosmetic composition for preventing or treating hair loss, or promoting hair growth, comprising a compound having the structure represented by the following Formula (I) or salt thereof; and at least one selected from the group comprising one or more nature-derived amino acid or salt thereof, one or more growth factor, noggin, one or more saturated or unsaturated C8 to C18 long chain fatty acid or salt thereof, one or more active factor and one or more water-soluble vitamin or salt thereof:

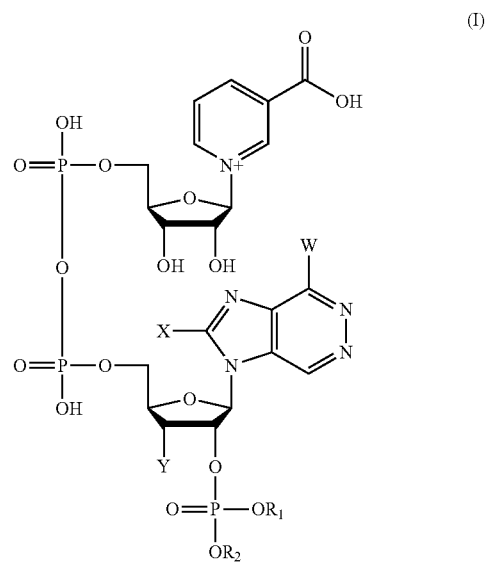

wherein, $R_1$ and $R_2$ are each independently H, $C_{1-4}$ alkyl which is unsubstituted or substituted with halogen, or —$CH_2$—CO—$CH_3$;

W is selected from the group consisting of $NH_2$, OH and SH;

X is selected from the group consisting of H, OH, SH, $NH_2$ and halogen; and

Y is selected from the group consisting of OH, H, $NH_2$ and halogen.

Advantageous Effects of Invention

The composition according to the present invention exhibits an excellent effect of preventing or treating hair loss and promoting hair growth, and can be safely used regardless of sex and age.

BRIEF DESCRIPTION OF DRAWINGS

FIG. 1 is a graph showing the results of cytotoxicity test in human hair dermal papilla cells according to Experimental Example 1.

FIG. 2 is a graph showing the test results for promotion of proliferation of human hair dermal papilla cells according to Experimental Example 2.

FIG. 3 is a graph showing the test results for the hair root production rate in the hair dermal papilla cells according to Experimental Example 3.

FIG. 4 is a graph showing the test results for the hair density according to Experimental Example 4.

FIG. 5 is a graph showing the measurement results of hair enlongation rate according to Experimental Example 5.

BEST MODE FOR CARRYING OUT THE INVENTION

The present invention is described in detail below.

The present invention is related to a pharmaceutical composition for preventing or treating hair loss, or promoting hair growth and a cosmetic composition for preventing or improving hair loss, or promoting hair growth, comprising a compound having the structure represented by the following Formula (I) or salt thereof; and at least one selected from the group comprising one or more nature-derived amino acid or salt thereof, one or more growth factor, noggin, one or more saturated or unsaturated C8 to C18 long chain fatty acid or salt thereof, one or more active factor and one or more water-soluble vitamin or salt thereof:

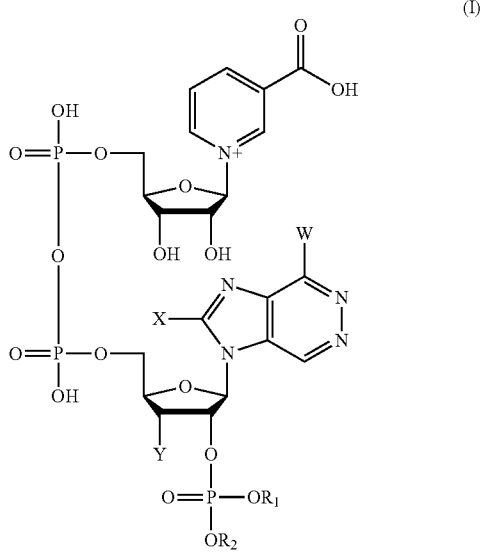

(I)

wherein, $R_1$ and $R_2$ are each independently H, $C_{1-4}$ alkyl which is unsubstituted or substituted with halogen, or —$CH_2$—CO—$CH_3$;

W is selected from the group consisting of $NH_2$, OH and SH;

X is selected from the group consisting of H, OH, SH, $NH_2$ and halogen; and

Y is selected from the group consisting of OH, H, $NH_2$ and halogen.

In one embodiment of the present invention, the compound of Formula (I) may be nicotinic acid adenine dinucleotide phosphate (NAADP), or a salt or derivative thereof. The NAADP used in the present invention is the one synthesized by CD38, i.e. ADP-ribosyl cyclase in a cell (Chini EN. et al., Biochem J 362:125-130, 2002; BERRIDGE G. et al., Biochem. J., 365: 295-301, 2002; Aarhus R. et al., J Biol Chem., 270(51): 30327-30333, 1995).

Further, the compound having the structure of Formula (I) used in the present invention may be provided as a free substance, as well as a pharmaceutically acceptable salt, solvate, polymorph, or prodrug thereof. Moreover, the salt of the compound having the structure of Formula (I) is not particularly limited as long as it is in a form that can be compounded in a medicine or cosmetics, and may include an inorganic salt or an organic salt and be an acidic salt or an alkaline salt. In particular, when the salt is formed by a cation, it may be alkali metal salts such as sodium salts or potassium salts; alkaline earth metal salts such as calcium salts, magnesium salts or barium salts; basic amino acid salts such as arginine and lysine; ammonium salts such as ammonium salts or tricyclohexylammonium salts; and various alkanolamine salts such as monoethanolamine salts, diethanolamine salts, triethanolamine salts, monoisopropanolamine salts, diisopropanolamine salts, and triisopropanolamine salts and the like. Preferably, the salt is an alkali metal salt, and more preferably, may be tetrasodium salt.

In one embodiment of the present invention, the amino acid may be selected from the group comprising alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine, and the salt of the amino acid is not limited as long as it is a pharmaceutically acceptable salt.

As used herein, the term "growth factor" refers to a polypeptide having a function of promoting division, growth and differentiation of various cells in a human body, and includes those obtained through gene recombination or extraction.

In one embodiment of the present invention, the growth factor may be selected from the group comprising an epithelial growth factor (EGF), an acidic fibroblast growth factor (FGF (a)), a basic fibroblast growth factor (FGF (b)), a vascular endothelial growth factor (VEGF), a platelet-derived growth factor (PDGF) and a keratinocyte growth factor (KGF).

As used herein, the term "noggin" refers to a protein that is involved in the development of nerve tissues, muscles, and bones among human tissues.

In one embodiment of the present invention, noggin may be obtained through a method known in the art.

In one embodiment of the present invention, although the long-chain fatty acid is not particularly limited as long as it is a saturated or unsaturated C8 to C18 long chain fatty acid, the long-chain fatty acid may be selected from the group comprising linolenic acid, myristic acid, oleic acid and palmitic acid, and the salt of the long-chain fatty acid is not particularly limited as long as it is pharmaceutically acceptable.

In one embodiment of the present invention, the active factor may be selected from the group comprising inositol, adenine, glutathione and cholesterol.

In one embodiment of the present invention, the water-soluble vitamins may be selected from the group comprising thiamine (B1), riboflavin (B2), niacinamide (B3), pantothenic acid (B5), pyridoxine (B6), biotin (B7), folic acid (B9), cyanocobalamin (B12) and ascorbic acid (C), and the salt of the water-soluble vitamin is not particularly limited as long as it is pharmaceutically acceptable.

In one embodiment of the present invention, the pharmaceutical or cosmetic composition promotes proliferation of hair dermal papilla cells, prolongs the life of hair dermal papilla cells, produces hair roots of hair dermal papilla cells, and increases density, thickness, or length of hair, or combination thereof, resulting in effects of prevention or treatment of hair loss, promotion of hair growth, and prevention or improvement of hair loss, which are demonstrated by the experimental examples disclosed herein.

In one embodiment of the present invention, the pharmaceutical or cosmetic composition may comprise the compound having the structure of Formula (I) above or salt thereof, one or more nature-derived amino acid or salt thereof, a mixture comprising one or more growth factor and noggin, one or more saturated or unsaturated C8 to C18 long chain fatty acid or salt thereof, one or more active factor selected from the group comprising inositol, adenine, glutathione and cholesterole, and one or more water-soluble vitamin or salt thereof.

In one embodiment of the present invention, the pharmaceutical composition or cosmetic composition may comprise the compound having the structure of Formula (I) above or salt thereof in an amount of 0.001 to 1% by weight based on the total weight of the composition.

In one embodiment of the present invention, the pharmaceutical composition or cosmetic composition may comprise the amino acid or salt thereof in an amount of 0.001 to 20% by weight based on the total weight of the composition, and this amount may be properly adjusted depending on a formulation and the conditions of production.

In one embodiment of the present invention, the pharmaceutical composition or cosmetic composition may comprise a mixture comprising the growth factor and noggin in an amount of 0.001 to 5% by weight, preferably 0.5 to 4% by weight, based on the total weight of the composition.

In one embodiment of the present invention, the pharmaceutical composition or cosmetic composition may comprise the long chain fatty acid or salt thereof in an amount of 0.001 to 5% by weight, preferably 0.2 to 1% by weight, based on the total weight of the composition.

In one embodiment of the present invention, the pharmaceutical composition or cosmetic composition may comprise the active factor in an amount of 0.001 to 5% by weight, preferably 0.1 to 0.5% by weight, based on the total weight of the composition.

In one embodiment of the present invention, the pharmaceutical composition or cosmetic composition may comprise the water-soluble vitamin or salt thereof in an amount of 0.001 to 5% by weight, preferably 0.2 to 1.2% by weight, based on the total weight of the composition.

In one embodiment of the present invention, the pharmaceutical composition or cosmetic composition may comprise the amino acid in an amount of 4000 parts by weight to 40000 parts by weight, preferably 16000 parts by weight to 40000 parts by weight, based on 100 parts by weight of the growth factor and noggin, the water-soluble vitamin or salt thereof in an amount of 240 parts by weight to 4000 parts by weight, preferably 1000 parts by weight to 4000 parts by weight, based on 100 parts by weight of the growth factor and noggin, the active factor in an amount of 80 parts by weight to 1600 parts by weight, preferably 160 parts by weight to 800 parts by weight, based on 100 parts by weight of the growth factor and noggin, the long chain fatty acid or salt thereof in an amount of 200 parts by weight to 3200 parts by weight, preferably 400 parts by weight to 1600 parts by weight, based on 100 parts by weight of the growth factor and noggin, and the growth factor and noggin in an amount of 6.25 parts by weight to 125 parts by weight, preferably 12.5 parts by weight to 50 parts by weight, based on 100 parts by weight of the active factor.

In one embodiment of the present invention, the growth factor comprises an epithelial growth factor (EGF), an acidic fibroblast growth factor (FGF (a)), a basic fibroblast growth factor (FGF (b)), a vascular endothelial growth factor (VEGF), a platelet-derived growth factor (PDGF) and a keratinocyte growth factor (KGF). Further, the weight ratio of epithelial growth factor (EGF): acidic fibroblast growth factor (FGF (a)): basic fibroblast growth factor (FGF (b)): vascular endothelial growth factor (VEGF): platelet-derived growth factor (PDGF): keratinocyte growth factor (KGF): noggin in the pharmaceutical or cosmetic composition may be 0.1 to 10:0.1 to 10:0.1 to 10:0.1 to 10:0.1 to 10:0.1 to 10:0.1 to 10, preferably 2 to 6:4 to 8:4 to 8:1 to 2:1 to 2:1 to 2:1 to 2, and more preferably 2 to 4:2 to 6:2 to 6:2 to 6:2 to 6:2 to 6:2 to 6.

In one embodiment of the present invention, the weight ratio of amino acid or salt thereof: long chain fatty acid or salt thereof: active factor: water-soluble vitamin or salt thereof in the pharmaceutical composition or cosmetic composition may be 100 to 2000:10 to 200:5 to 200:10 to 200.

In one embodiment of the present invention, the composition may further comprise suitable carriers, excipients and diluents conventionally used in the manufacture of pharmaceutical compositions or cosmetic compositions.

In particular, the composition is formulated using excipients or diluents such as pharmaceutically acceptable fillers, extenders, binders, humectants, disintegrants, surfactants and the like which are generally used. In addition, anticoagulants, lubricants, fragrances, emulsifiers, preservatives, and the like may be added, and the composition may be formulated using methods well known in the art to provide rapid, sustained, or delayed release of the active ingredient after administration to the mammal.

The pharmaceutical composition according to the present invention may be formulated into a conventional pharmaceutical formulation known in the art, and preferably it may be formulated into a transdermal preparation and an external preparation for skin for topical application.

In one embodiment of the present invention, the pharmaceutical composition according to the present invention may be an external preparation for skin, and can be formulated into any possible formulations applicable to skin, especially, scalp, such as ointment, paste, gel, jelly, serum, aerosol spray, non-aerosol spray, foam, cream, lotion, solution or suspension.

The composition according to the present invention can be administered by topical application once or twice a day to a site where prevention or treatment of hair loss, or promotion of hair growth is desired. The daily application amount of the composition is about 0.5 to 3 mg/cm$^2$ (skin surface area) based on 1 wt % of the active ingredient, and may be increased or decreased depending on the area of the application site. The dose and the frequency of administration can be appropriately increased or decreased according to the patient's age, sex, and degree of progress of hair loss.

On the other hand, the cosmetic composition according to the present invention may be applied in any possible formulations applied to the skin, particularly scalp. More specifically, the composition may be prepared in a formulation such as a hair tonic, a hair conditioner, a hair essence, a hair lotion, a hair nutrition lotion, a hair shampoo, a hair rinse, a hair treatment, a hair cream, a hair nutrition cream, a hair moisturizing cream, a hair massage cream, a hair wax, a hair aerosol, a hair pack, a hair nutrition pack, a hair soap, a hair cleansing foam, a hair oil, a hair drying agent, an agent for preserving hair, a hair dye, a hair waving agent, a hair bleaching agent, a hair gel, a hair glaze, a hair dressinger, a hair lacquer, a hair moisturizer, a hair mousse or a hair spray. In addition, it can also be prepared as a skin-contacting substance that comes into contact with a skin, such as cosmetics, detergents, and fibers.

In one embodiment of the present invention, the components of the cosmetic composition can be appropriately selected and blended by those skilled in the art within a range not to impair the purposes and effects of the present invention. Examples of the compounding ingredients that can be added include an oil and fat component, a moisturizer, an emollient, a surfactant, organic and inorganic pigments, an organic powder, an ultraviolet absorber, a preservative, a bactericide, an antioxidant, a plant extract, a pH adjuster, an alcohol, a dye, fragrances, a blood circulation promoter, a skin cooling agent, an anhydrotics, purified water and the like.

MODE FOR THE INVENTION

Hereinafter, the present invention will be described in more detail by way of examples. It will be apparent to those skilled in the art that the following examples are illustrative only and various changes and modifications may be made without departing from the spirit and scope of the invention, and such changes and modifications are also within the scope of the appended claims.

EXAMPLES

Preparation Example 1. Preparation of a Mixture Comprising a Growth Factor and Noggin An ephithelial growth factor (EGF), an acidic fibroblast growth factor (FGF (a)), a basic fibroblast growth factor (FGF (b)), a vascular endothelial growth factor (VEGF), a platelet-derived growth factor (PDGF), a keratinocyte growth factor (KGF), and Noggin were mixed in a composition shown in Table 1 below and then prepared into liposomes using a high-speed homogenizer (Preparation Examples (1-1) to (1-5)). The growth factors and Noggin were synthesized by transforming *E. coli* with human-derived genes, and their contents were measured by SDS-PAGE and HPLC. The growth factors and proteins were prepared in accordance with the criteria for the use in cosmetics or pharmaceuticals of Korean Ministry of Food and Drug Safety and INCI [International nomenclature cosmetic ingredient] of US PCPC (Personal care products councils).

TABLE 1

| (Unit: mg) | EGF | FGF(a) | FGF(b) | VEGF | PDGF | KGF | Noggin |
|---|---|---|---|---|---|---|---|
| Preparation Example(1-1) | 1 | 1.5 | 1.5 | 0.25 | 0.25 | 0.25 | 0.25 |
| Preparation Example(1-2) | 0.5 | 1 | 1 | 0.5 | 0.5 | 0.5 | 0.5 |
| Preparation Example(1-3) | 1 | 0.5 | 0.5 | 0.25 | 0.25 | 1 | 1 |
| Preparation Example(1-4) | 0.5 | 1 | 1 | 0.5 | 0.5 | 0.25 | 0.25 |
| Preparation Example(1-5) | 1 | 0.5 | 0.5 | 0.25 | 0.25 | 0.5 | 0.5 |

Preparation Example 2. Preparation of a Mixture of Nutrients

Amino acids, long chain fatty acids, active factors and water-soluble vitamins were mixed in the compositions shown in Table 2 below, and then prepared into liposomes using a high-speed homogenizer. (Preparation Examples (2-1) to (2-5)). The amino acids, long chain fatty acids, active factors and water-soluble vitamins were prepared in accordance with the criteria for the use in cosmetics or pharmaceuticals of Korean Ministry of Food and Drug Safety. In the case of amino acids, 20 amino acids derived from nature were evenly blended on the basis of weight, and vitamins, active factors and fatty acids were also blended evenly on the basis of weight. Standard error for each component was less than 10%.

TABLE 2

| component(unit: mg) | Preparation Example(2-1) | Preparation Example(2-2) | Preparation Example(2-3) | Preparation Example(2-4) | Preparation Example(2-5) |
|---|---|---|---|---|---|
| Alanine | 400 | 600 | 800 | 1000 | 1200 |
| Arginine HCl | | | | | |
| Asparagine | | | | | |
| Aspartic acid | | | | | |
| Cysteine HCl | | | | | |
| Glutamic acid | | | | | |
| Glutamine | | | | | |
| Glycine | | | | | |
| Histidine HCl | | | | | |
| Isoleucine | | | | | |
| Leucine | | | | | |

TABLE 2-continued

| component(unit: mg) | Preparation Example(2-1) | Preparation Example(2-2) | Preparation Example(2-3) | Preparation Example(2-4) | Preparation Example(2-5) |
|---|---|---|---|---|---|
| Lysine HCl | | | | | |
| Methionine | | | | | |
| Phenylalanine | | | | | |
| Proline | | | | | |
| Serine | | | | | |
| Threonine | | | | | |
| Tryptophan | | | | | |
| Tyrosine | | | | | |
| Valine | | | | | |
| Biotin(B7) | 20 | 30 | 40 | 50 | 60 |
| Ascorbic acid(C) | 5 | 6 | 7 | 8 | 9 |
| Niacinamide(B3) | | | | | |
| Calcium pantothenate(B5) | | | | | |
| Pyridoxine HCl(B6) | | | | | |
| Riboflavin(B2) | | | | | |
| Thiamin HCl(B1) | | | | | |
| Cyanocobalamin(B12) | | | | | |
| Inositol | 10 | 20 | 40 | 60 | 100 |
| Adenine | | | | | |
| Glutathione | | | | | |
| Cholesterole | | | | | |
| Linolenic acid | 20 | 40 | 60 | 80 | 100 |
| Myristic acid | | | | | |
| Oleic acid | | | | | |
| Palmitic acid | | | | | |

Comparative Preparation Example 1. NAADP Liposome Solution

NAADP was prepared according to the method described in "Acidic residues at the active sites of CD38 and ADP-ribosyl cyclase determine nicotinic acid adenine dinucleotide phosphate (NAADP) synthesis and hydrolysis activities". The Journal of Biological Chemistry. 281 (39): 28951-7, using NADP (nicotinamide adenine dinucleotide phosphate), nicotinic acid (NA) and ADP-ribosyl cyclase purchased from Sigma-Aldrich (USA).

The prepared NAADP was prepared into liposomes using a medium prepared by mixing phospholipids, lecithin, oleic acid, and caprylyl glycol in a ratio of 1:1:0.05:0.05, and a high-speed homogenizer.

Examples 1 to 9. Preparation of Mixtures

A mixture comprising the mixture of Preparation Example 1 and the mixture of Preparation Example 2 in the composition shown in Table 3 below was prepared by a known method. Specifically, the mixture of Preparation Example 1 was added to 1 L of purified water by the weight indicated in Table 1, and the mixture of Preparation Example 2 was added thereto by two times the weight indicated in Table 2 above.

TABLE 3

| | NAADP | Preparation Example(1-1) | Preparation Example(1-2) | Preparation Example(1-3) | Preparation Example(2-1) | Preparation Example(2-2) | Preparation Example(2-3) |
|---|---|---|---|---|---|---|---|
| Comparative Preparation Example 1 | ○ | — | — | — | — | — | — |
| Example 1 | ○ | ○ | | | ○ | | |
| Example 2 | ○ | | ○ | | | ○ | |
| Example 3 | ○ | | | ○ | | | ○ |
| Example 4 | ○ | ○ | | | | ○ | |
| Example 5 | ○ | ○ | | | | | ○ |
| Example 6 | ○ | | | ○ | ○ | | |
| Example 7 | ○ | | | ○ | | | ○ |
| Example 8 | ○ | | | | ○ | ○ | |
| Example 9 | ○ | | | ○ | | ○ | |

Example 10. Preparation of a Mixture

A mixture was prepared in the same manner as in Example 1, except that the amount of Preparation Example (1-1) was changed to 0.25 times.

Example 11. Preparation of a Mixture

A mixture was prepared in the same manner as in Example 1, except that the amount of Preparation Example (1-1) was changed to 0.5 times.

Example 12. Preparation of a Mixture

A mixture was prepared in the same manner as in Example 1, except that the amount of Preparation Example (1-1) was changed to 2 times.

Example 13. Preparation of a Mixture

A mixture was prepared in the same manner as in Example 1, except that the amount of Preparation Example (1-1) was changed to 5 times.

Example 14. Preparation of a Mixture

A mixture was prepared in the same manner as in Example 1, except that the added amount of the amino acid was changed to 200 mg.

Example 15. Preparation of a Mixture

A mixture was prepared in the same manner as in Example 1, except that the added amount of the amino acid was changed to 400 mg.

Example 16. Preparation of a Mixture

A mixture was prepared in the same manner as in Example 1, except that the added amount of the amino acid was changed to 1600 mg.

Example 17. Preparation of a Mixture

A mixture was prepared in the same manner as in Example 1, except that the added amount of the amino acid was changed to 2000 mg.

Example 18. Preparation of a Mixture

A mixture was prepared in the same manner as in Example 1, except that the added amount of the water-soluble vitamins including biotin was changed to 12 mg.

Example 19. Preparation of a Mixture

A mixture was prepared in the same manner as in Example 1, except that the added amount of the water-soluble vitamins including biotin was changed to 24 mg.

Example 20. Preparation of a Mixture

A mixture was prepared in the same manner as in Example 1, except that the added amount of the water-soluble vitamins including biotin was changed to 100 mg.

Example 21. Preparation of a Mixture

A mixture was prepared in the same manner as in Example 1, except that the added amount of the water-soluble vitamins including biotin was changed to 200 mg.

Example 22. Preparation of a Mixture

A mixture was prepared in the same manner as in Example 1, except that the added amount of the active factor was changed to 4 mg.

Example 23. Preparation of a Mixture

A mixture was prepared in the same manner as in Example 1, except that the added amount of the active factor was changed to 8 mg.

Example 24. Preparation of a Mixture

A mixture was prepared in the same manner as in Example 1, except that the added amount of the active factor was changed to 40 mg.

Example 25. Preparation of a Mixture

A mixture was prepared in the same manner as in Example 1, except that the added amount of the active factor was changed to 80 mg.

Example 26. Preparation of a Mixture

A mixture was prepared in the same manner as in Example 1, except that the added amount of the long chain fatty acid was changed to 10 mg.

Example 27. Preparation of a Mixture

A mixture was prepared in the same manner as in Example 1, except that the added amount of the long chain fatty acid was changed to 20 mg.

Example 28. Preparation of a Mixture

A mixture was prepared in the same manner as in Example 1, except that the added amount of the long chain fatty acid was changed to 80 mg.

Example 29. Preparation of a Mixture

A mixture was prepared in the same manner as in Example 1, except that the added amount of the long chain fatty acid was changed to 160 mg.

Formulation Example

Compositions according to Comparative Formulation Examples 1 and 2 and Formulation Examples 1 and 2 were prepared with the composition according to Table 4 below. However, the following formulation examples are intended to illustrate rather than limit the present invention.

TABLE 4

| (Weight %) | Comparative Formulation Example 1 | Comparative Formulation Example 2 | Formulation Example 1 | Formulation Example 2 |
|---|---|---|---|---|
| Purified water | 52.9 | 51.9 | 41.9 | 40.9 |
| Glycerine | 3 | 3 | 3 | 3 |
| EDTA-Na | 0.05 | 0.05 | 0.05 | 0.05 |
| Amisoft CS-22 | 30 | 30 | 30 | 30 |
| Miconate LES | 12 | 12 | 12 | 12 |
| Citric acid | 0.1 | 0.1 | 0.1 | 0.1 |
| Phenoxyethanol | 0.7 | 0.7 | 0.7 | 0.7 |
| Ethylhexyl glycerin | 0.05 | 0.05 | 0.05 | 0.05 |

TABLE 4-continued

| (Weight %) | Comparative Formulation Example 1 | Comparative Formulation Example 2 | Formulation Example 1 | Formulation Example 2 |
|---|---|---|---|---|
| Preparation Example 1-1 | — | — | 1 | 2 |
| Preparation Example 2-1 | — | — | 10 | 10 |
| NAADP | — | 0.1 | 0.1 | 0.1 |
| NaCl | 1 | 1 | 1 | 1 |
| Perfume | 0.2 | 0.2 | 0.2 | 0.2 |
| Total | 100 | 100 | 100 | 100 |

Experimental Examples

Experimental Examples 1. Cytotoxicity Test in Human Hair Dermal Papilla Cells

To confirm cytotoxicity in human hair dermal papilla cells (HHDPC), MTT assay which determines cytotoxicity by measuring mitochondrial reducing power by dehydrogenase action was conducted.

Human hair dermal papilla cells were cultured in an HDP kit medium (Human hair dermal papilla cell media kit) at 37° C. in a 5% $CO_2$ incubator (manufactured by Thermo Fisher Scientific, USA).

The cultured cells were dispensed into a 24-well plate at a concentration of $3 \times 10^4$ cells/well. After 18 hours, the mixtures according to Preparation Examples (1-1) to (1-5) and the mixtures according to Preparation Example (2-1) to (2-5) were added to each well at concentrations of 50 µg/ml, 100 µg/ml and 200 µg/ml, respectively. Then, the cells were cultured in the 5% $CO_2$ incubator at 37° C. for 48 hours. After 48 hours of incubation, each well was washed once with PBS (phosphate buffered saline) solution, and added with 50 µl of 5 g/mL MTT reagent (Sigma, USA) and 450 µl of fresh medium. The wells were incubated for 2.5 hours and then supernatants were removed. As formazan crystals were observed in each well, DMSO (dimethylsulfoxide) was added and shaken for 30 minutes in the dark to dissolve the formazan crystal, and then the absorbance was measured at 750 nm using a spectrophotometer.

The results of the measurement are shown in Table 5 and FIG. 1, and it was confirmed that no toxicity was observed regardless of the treatment concentration.

TABLE 5

|  | 50 µg/ml | 100 µg/ml | 200 µg/ml |
|---|---|---|---|
| Preparation Example 1-1 | 98 | 97 | 95 |
| Preparation Example 1-2 | 99 | 96 | 95 |
| Preparation Example 1-3 | 100 | 97 | 97 |
| Preparation Example 1-4 | 100 | 98 | 96 |
| Preparation Example 1-5 | 100 | 99 | 95 |
| Preparation Example 2-1 | 100 | 99 | 98 |
| Preparation Example 2-2 | 100 | 100 | 98 |
| Preparation Example 2-3 | 100 | 100 | 95 |
| Preparation Example 2-4 | 100 | 100 | 99 |
| Preparation Example 2-5 | 100 | 100 | 95 |

Experimental Example 2. Comparison of Cell Proliferation Efficacy in Human Hair Dermal Papilla Cells For comparison of cell proliferation efficacy, 100 µg/ml of each mixture according to Examples 1 to 9 and 1 µM NAADP solution according to Comparative Preparation Example 1 were tested in the same manner as in Experimental Example 1. The results are shown in Table 6 below and FIG. 2.

Cell growth rate was better at the treatment of the mixtures according to Examples 1 to 9 than the treatment of the NAADP solution according to Comparative Preparation Example 1, and differentially increased cell proliferation was confirmed. In particular, Examples 1, 4, and 5, which include the mixture according to Preparation Example (1-1), exhibited more excellent efficacy for cell proliferation.

TABLE 6

|  | Growth rate(%) |
|---|---|
| Comparative Preparation Example 1 | 20 |
| Example 1 | 55 |
| Example 2 | 47 |
| Example 3 | 41 |
| Example 4 | 51 |
| Example 5 | 54 |
| Example 6 | 45 |
| Example 7 | 46 |
| Example 8 | 41 |
| Example 9 | 39 |

Experimental Example 3. Test of Hair Root Production Rate in Human Hair Dermal Papilla Cells The production rate of hair roots required for hair production was measured in human hair dermal papilla cells. The hair dermal papilla cells were cultured by the method described in Experimental Example 1 and then tested. The cultured hair dermal papilla cells were treated with the mixtures according to Examples 1, 4 and 5 and the NAADP solution according to Comparative Preparation Example 1 at concentrations of 50 µg/ml, 100 µg/ml and 200 µg/ml, respectively, and the numbers of hair roots were measured with a microscope. The results are shown in Table 7 below and FIG. 3. The yields of the hair roots were higher in the groups treated with mixtures according to Examples 1, 4 and 5 than the group treated with NAADP solution of Comparative Example 1.

TABLE 7

|  | 50 µg/ml | 100 µg/ml | 200 µg/ml |
|---|---|---|---|
| untreated group | 10 | 11 | 9 |
| Comparative Preparation Example 1 | 13 | 21 | 23 |

TABLE 7-continued

| | 50 μg/ml | 100 μg/ml | 200 μg/ml |
|---|---|---|---|
| Example 1 | 55 | 62 | 81 |
| Example 4 | 51 | 53 | 78 |
| Example 5 | 45 | 55 | 74 |

Unit: number of hair roots

Experimental Example 4. Test of Hair Density in Human Body

A test for the application of the composition of the present invention to human body was conducted, which was conducted according to a guideline provided by Korea Ministry of Food & Drug Safety. The test was conducted for 24 weeks, and men and women diagnosed with androgenetic alopecia aged 18 to 54 years were selected as test subjects. Twenty subjects were assigned to a test group and a control group, respectively. The compositions of Formulation Examples 1 and 2 and Comparative Formulation Example 2 were applied for 24 weeks for the test group. The composition of Comparative Formulation Example 1 was applied for 24 weeks for the control group. And then hair densities were measured. The hair density was evaluated as a score of 1 to 10, and the results are shown in Table 8 below and FIG. 4. The density score for the composition of Comparative Formulation Example 1 was 2 or less even at week 24. The density score for the composition of Comparative Formulation Example 2 was higher than the score for the composition of Comparative Formulation Example 1, but was lower than the scores for the compositions of Formulation Examples 1 and 2. The compositions of Formulation Examples 1 and 2 showed better evaluation scores than the compositions of Comparative Formulation Examples 1 and 2, with an average score of 8 or higher. From these results, it was found that Formulation Examples 1 and 2 improved hair densities more than Comparative Formulation Examples 1 and 2.

TABLE 8

| | Week 6 | Week 12 | Week 24 |
|---|---|---|---|
| Comparative Formulation Example 1 | 1 | 2 | 2 |
| Comparative Formulation Example 2 | 3 | 5 | 6 |
| Formulation Example 1 | 5 | 8 | 9 |
| Formulation Example 2 | 6 | 9 | 10 |

Unit: score

Experimental Example 5. Test of Hair Elongation Rate in Human Body

A test was conducted in the same manner as in Experimental Example 4 above. The elongation rate of hair was measured as the relative elongation rate for each week at weeks 6, 12, and 24. The results are shown in Table 9 below and FIG. 5. It was found that the compositions of Formulation Examples 1 and 2 improved the elongation rate by about 20 to 30% compared to the composition of Comparative Formulation Example 1. In addition, while the maximum enlongation rates of the compositions of Comparative Formulation Example 1 and Comparative Formulation Example 2 were limited to about 50% and about 70%, respectively, the compositions of Formulation Examples 1 and 2 exhibited an elongation rate of about 130%.

TABLE 9

| | Week 6 | Week 12 | Week 24 |
|---|---|---|---|
| Comparative Formulation Example 1 | 25 | 39 | 47 |
| Comparative Formulation Example 2 | 40 | 50 | 67 |
| Formulation Example 1 | 81 | 120 | 130 |
| Formulation Example 2 | 79 | 111 | 126 |

Experimental Example 6. Comparison of Efficacies for Cell Proliferation in Human Hair Dermal Papilla Cells For comparison of efficacies for cell proliferation, a test was conducted in the same manner as in Experimental Example 1 for 100 μg/ml of each mixture according to Example 1 and Examples 10 to 25, and the results are shown in Table 10 below. The degree of cell proliferation when hair dermal papilla cells were treated with the mixture of Example 1 was set as a reference (set at 100), and the degree of cell proliferation when the hair dermal papilla cells were treated with the mixtures of Examples 10 to 25 was expressed as a relative value compared to the reference.

TABLE 10

| | Values |
|---|---|
| Example 1 | 100 |
| Example 10 | 22 |
| Example 11 | 72 |
| Example 12 | 81 |
| Example 13 | 53 |
| Example 14 | 17 |
| Example 15 | 59 |
| Example 16 | 87 |
| Example 17 | 75 |
| Example 18 | 11 |
| Example 19 | 55 |
| Example 20 | 91 |
| Example 21 | 63 |
| Example 22 | 52 |
| Example 23 | 83 |
| Example 24 | 98 |
| Example 25 | 54 |
| Example 26 | 8 |
| Example 27 | 76 |
| Example 28 | 78 |
| Example 29 | 32 |

As shown in the above results, the composition of the present invention improved the proliferation, activity and longevity of the hair dermal papilla cells at the experiment level of cells and also showed a high production rate of hair roots. In addition, clinical trials showed excellent increase in hair density and thickness and hair elongation efficacy. In particular, it was confirmed that the above effects were significantly higher in quantity than that of the composition containing only NAADP.

It was also confirmed that the composition of the present invention exhibits more excellent proliferation activity for hair dermal papilla cells when the content ratio of each component is within a specific value range.

For example, it was confirmed that the effect was excellent when the content of the amino acids was 4,000 to 40,000 parts by weight, particularly 16,000 to 40,000 parts by weight based on 100 parts by weight of the growth factors and noggin.

In addition, it was confirmed that the effect was excellent when the content of the water-soluble vitamins including biotin was 240 to 4,000 parts by weight, particularly 1,000 to 4,000 parts by weight based on 100 parts by weight of the growth factors and noggin.

In addition, it was confirmed that the effect was excellent when the content of the active factor was 80 to 1,600 parts by weight, particularly 160 to 800 parts by weight based on 100 parts by weight of the growth factors and noggin.

In addition, it was confirmed that the effect was excellent when the content of the long chain fatty acid was 200 to 3,200 parts by weight, particularly 400 to 1,600 parts by weight based on 100 parts by weight of the growth factors and noggin.

In addition, it was confirmed that the effect was excellent when the content of the growth factor and noggin were 6.25 to 125 parts by weight, particularly 12.5 to 50 parts by weight based on 100 parts by weight of the activating factor.

The invention claimed is:

1. A pharmaceutical composition for treating hair loss, or promoting hair growth, comprising:
   a compound having a structure represented by the following Formula (I) or salt thereof; and
   at least one selected from the group consisting of one or more naturally occurring amino acid or salt thereof, one or more growth factor, noggin, one or more saturated or unsaturated C8 to C18 long chain fatty acid or salt thereof, one or more active factor and one or more water-soluble vitamin or salt thereof:

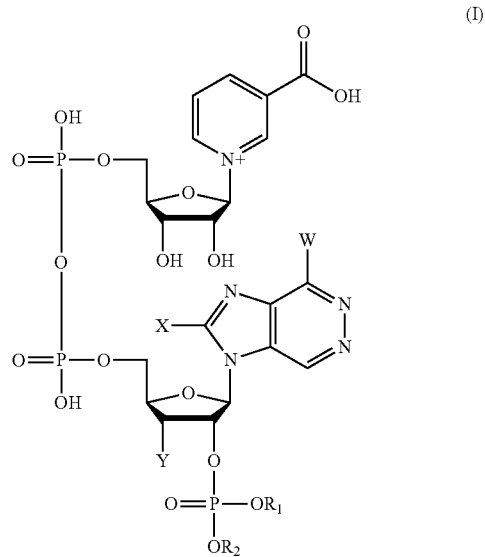

wherein,
$R_1$ and $R_2$ are each independently H, $C_{1-4}$ alkyl which is unsubstituted or substituted with halogen, or —$CH_2$—CO—$CH_3$;
W is selected from the group consisting of $NH_2$, OH and SH;
X is selected from the group consisting of H, OH, SH, $NH_2$ and halogen; and
Y is selected from the group consisting of OH, H, $NH_2$ and halogen,
wherein the active factor is selected from the group consisting of inositol, adenine, glutathione and cholesterol.

2. The pharmaceutical composition according to claim 1, wherein the compound of Formula (I) is nicotinic acid adenine dinucleotide phosphate (NAADP).

3. The pharmaceutical composition according to claim 1, wherein the amino acid is selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

4. The pharmaceutical composition according to claim 1, wherein the one or more growth factor is selected from the group consisting of an epithelial growth factor (EGF), an acidic fibroblast growth factor (FGF (a)), a basic fibroblast growth factor (FGF (b)), a vascular endothelial growth factor (VEGF), a platelet-derived growth factor (PDGF) and a keratinocyte growth factor (KGF).

5. The pharmaceutical composition according to claim 1, wherein the long-chain fatty acid is selected from the group consisting of linolenic acid, myristic acid, oleic acid and palmitic acid.

6. The pharmaceutical composition according to claim 1, wherein the water-soluble vitamin is selected from the group consisting of thiamine (B1), riboflavin (B2), niacinamide (B3), pantothenic acid or salt thereof (B5), pyridoxine (B6), biotin (B7), folic acid (B9), cyanocobalamin (B12) and ascorbic acid (C).

7. The pharmaceutical composition according to claim 1, wherein the composition promotes proliferation of hair dermal papilla cells.

8. The pharmaceutical composition according to claim 1, wherein the composition prolongs the life of hair dermal papilla cells.

9. The pharmaceutical composition according to claim 1, wherein the composition produces hair roots of hair dermal papilla cells.

10. The pharmaceutical composition according to claim 1, wherein the composition increases density, thickness, or length of hair, or combination thereof.

11. The pharmaceutical composition according to claim 1, wherein the composition comprises:
    the compound having the structure of Formula (I) or salt thereof;
    one or more naturally occurring amino acid or salt thereof;
    a mixture comprising one or more growth factor and noggin;
    one or more saturated or unsaturated C8 to C18 long chain fatty acid or salt thereof;
    one or more active factor selected from the group consisting of inositol, adenine, glutathione and cholesterol; and
    one or more water-soluble vitamin or salt thereof.

12. The pharmaceutical composition according to claim 11, wherein the composition comprises the compound having the structure of Formula (I) or salt thereof in an amount of 0.001 to 1% by weight, the amino acid or salt thereof in an amount of 0.001 to 20% by weight, the mixture comprising the growth factor and noggin in an amount of 0.001 to 5% by weight, the long chain fatty acid or salt thereof in an amount of 0.001 to 5% by weight, the active factor in an amount of 0.001 to 5% by weight, and the water-soluble vitamin or salt thereof in an amount of 0.001 to 5% by weight, based on the total weight of the composition.

13. The pharmaceutical composition according to claim 11, wherein the growth factor comprises an epithelial growth factor (EGF), an acidic fibroblast growth factor (FGF (a)), a basic fibroblast growth factor (FGF (b)), a vascular endothelial growth factor (VEGF), a platelet-derived growth factor (PDGF) and a keratinocyte growth factor (KGF), and the weight ratio of epithelial growth factor (EGF): acidic fibroblast growth factor (FGF (a)): basic fibroblast growth factor (FGF (b)): vascular endothelial growth factor (VEGF): platelet-derived growth factor (PDGF): keratinocyte growth factor (KGF): noggin in the composition is 0.1 to 10:0.1 to 10:0.1 to 10:0.1 to 10:0.1 to 10: 0.1 to 10:0.1 to 10.

14. The pharmaceutical composition according to claim 13, wherein the growth factors and noggin are comprised in the composition so that the weight ratio of epithelial growth factor (EGF): acidic fibroblast growth factor (FGF (a)): basic fibroblast growth factor (FGF (b)): vascular endothelial growth factor (VEGF): platelet-derived growth factor (PDGF): keratinocyte growth factor (KGF): noggin is 2 to 6:4 to 8:4 to 8:1 to 2:1 to 2:1 to 2.

15. The pharmaceutical composition according to claim 14, wherein the growth factors and noggin are comprised in the composition so that the weight ratio of epithelial growth factor (EGF): acidic fibroblast growth factor (FGF (a)): basic fibroblast growth factor (FGF (b)): vascular endothelial growth factor (VEGF): platelet-derived growth factor (PDGF): keratinocyte growth factor (KGF): noggin is 2 to 4:2 to 6:2 to 6:2 to 6:2 to 6:2 to 6.

16. The pharmaceutical composition according to claim 11, wherein the weight ratio of amino acid or salt thereof: long chain fatty acid or salt thereof: active factor: water-soluble vitamin or salt thereof in the composition is 100 to 2000:10 to 200:5 to 200:10 to 200.

17. The pharmaceutical composition according to claim 11, wherein the composition comprises:
the amino acid in an amount of 4000 parts by weight to 40000 parts by weight based on 100 parts by weight of the growth factor and noggin,
the water-soluble vitamin or salt thereof in an amount of 240 parts by weight to 4000 parts by weight based on 100 parts by weight of the growth factor and noggin,
the active factor in an amount of 80 parts by weight to 1600 parts by weight based on 100 parts by weight of the growth factor and noggin,
the long chain fatty acid or salt thereof in an amount of 200 parts by weight to 3200 parts by weight based on 100 parts by weight of the growth factor and noggin, and
the growth factor and noggin in an amount of 6.25 parts by weight to 125 parts by weight based on 100 parts by weight of the active factor.

18. The pharmaceutical composition according to claim 1, wherein the composition is in the form of an ointment, paste, gel, jelly, serum, aerosol spray, non-aerosol spray, foam, cream, lotion, solution or suspension.

* * * * *